(12) United States Patent
Kim et al.

(10) Patent No.: US 9,955,873 B2
(45) Date of Patent: May 1, 2018

(54) PHOTOACOUSTIC PROBE AND PHOTOACOUSTIC DIAGNOSTIC APPARATUS

(71) Applicants: SAMSUNG MEDISON CO., LTD., Gangwon-Do (KR); SAMSUNG ELECTRONICS CO., LTD., Suwon-si, Gyeonggi-do (KR)

(72) Inventors: Jung-ho Kim, Seoul (KR); Dal-kwon Koh, Suwon-si (KR); Jung-taek Oh, Seoul (KR); Jong-kyu Jung, Seoul (KR)

(73) Assignees: Samsung Medison Co., Ltd., Hongcheon-gun, Gangwon-do (KR); Samsung Electronics Co., Ltd., Suwon-si, Gyeonggi-do (KR)

( * ) Notice: Subject to any disclaimer, the term of this patent is extended or adjusted under 35 U.S.C. 154(b) by 288 days.

(21) Appl. No.: 14/293,090

(22) Filed: Jun. 2, 2014

(65) Prior Publication Data
US 2015/0164337 A1 Jun. 18, 2015

(30) Foreign Application Priority Data
Dec. 16, 2013 (KR) .......................... 10-2013-0156646

(51) Int. Cl.
*A61B 5/00* (2006.01)
(52) U.S. Cl.
CPC .................................. *A61B 5/0095* (2013.01)
(58) Field of Classification Search
CPC .................................................. A61B 5/0095
See application file for complete search history.

(56) References Cited

U.S. PATENT DOCUMENTS

| | | | |
|---|---|---|---|
| 6,128,123 A | 10/2000 | Wagner | |
| 6,168,278 B1 | 1/2001 | Mukai | |
| 7,202,852 B2 | 4/2007 | Harvie | |
| 7,859,660 B2 | 12/2010 | Slater | |
| 2002/0190262 A1* | 12/2002 | Nitta | ................... H01L 25/0753 257/99 |
| 2005/0045189 A1 | 3/2005 | Jay | |
| 2006/0244961 A1 | 11/2006 | Cole et al. | |

(Continued)

FOREIGN PATENT DOCUMENTS

| | | |
|---|---|---|
| JP | 2001-337356 A | 12/2001 |
| JP | 2006-317702 A | 11/2006 |

(Continued)

OTHER PUBLICATIONS

Search Report dated Sep. 1, 2014 issued in International Patent Application No. PCT/KR2014/003464.

(Continued)

*Primary Examiner* — Tse Chen
*Assistant Examiner* — Jason Ip
(74) *Attorney, Agent, or Firm* — McDermott Will & Emery LLP (57) ABSTRACT

Provided are a photoacoustic probe and photoacoustic diagnostic apparatus. The photoacoustic probe includes a light irradiation unit for irradiating first light that is used for photoacoustic imaging on an object and an indicator for providing information about whether the first light is irradiated by using the first light.

16 Claims, 7 Drawing Sheets

(56) References Cited

U.S. PATENT DOCUMENTS

| | | | |
|---|---|---|---|
| 2008/0037600 A1* | 2/2008 | Ma | G02F 1/3501 372/21 |
| 2008/0206886 A1* | 8/2008 | Wang | A61K 49/0021 436/172 |
| 2009/0054804 A1* | 2/2009 | Gharib | A61B 5/04001 600/554 |
| 2009/0177143 A1* | 7/2009 | Markle | A61B 5/14532 604/66 |
| 2011/0105867 A1 | 5/2011 | Schultz et al. | |
| 2011/0147566 A1* | 6/2011 | Furuya | G02F 1/37 250/205 |
| 2012/0236314 A1* | 9/2012 | Fermann | G02F 1/365 356/479 |
| 2013/0060122 A1 | 3/2013 | Zharov | |
| 2013/0261426 A1* | 10/2013 | Irisawa | A61B 5/0095 600/407 |
| 2013/0331681 A1 | 12/2013 | Tokita et al. | |
| 2013/0338478 A1* | 12/2013 | Hirota | A61B 8/429 600/407 |

FOREIGN PATENT DOCUMENTS

| | | |
|---|---|---|
| JP | 2012-205885 A | 10/2012 |
| WO | 02061405 A3 | 8/2002 |
| WO | 2004/042382 A1 | 5/2004 |
| WO | 2006/073408 A3 | 7/2006 |

OTHER PUBLICATIONS

Extended European Search Report for European Application No. EP14872760.5, dated Jul. 19, 2017.

* cited by examiner

PHOTOACOUSTIC PROBE AND PHOTOACOUSTIC DIAGNOSTIC APPARATUS

RELATED APPLICATIONS

This application claims the benefit of Korean Patent Application No. 10-2013-0156646, filed on Dec. 16, 2013, in the Korean Intellectual Property Office, the disclosure of which is incorporated herein in its entirety by reference.

BACKGROUND

1. Field

One or more embodiments of the present invention relate to a photoacoustic probe and a photoacoustic diagnostic apparatus including the same for use in diagnosis from photoacoustic images.

2. Description of the Related Art

A photoacoustic imaging technology uses a photoacoustic effect to noninvasively image biological tissues. When a biological tissue is irradiated with a short electromagnetic laser pulse for photoacoustic imaging, some of the energy of the laser pulse is absorbed into the biological tissue and converted into heat, thereby causing thermo-elastic expansion. The thermo-elastic expansion leads to emission of wideband ultrasound waves, and the emitted ultrasound waves are detected by ultrasound transducers from different directions and reconstructed into images.

Since photoacoustic imaging is based on the conversion of electrical signals into ultrasound waves for detection, this method has advantages of combining properties of optical imaging with those of ultrasound imaging. Pure optical imaging has much higher resolution than ultrasound imaging, but permits only limited imaging up to a predetermined depth from a surface of a living tissue due to strong optical scattering of soft tissues. On the other hand, ultrasound imaging provides a sufficiently high spatial resolution so as to examine a fetus. Photoacoustic imaging overcomes the drawback of optical imaging such as low imaging depths with conversion into ultrasound waves due to a photoacoustic effect, thereby achieving both a high optical contrast ratio and a high spatial resolution.

Photoacoustic imaging techniques have already been developed significantly to conduct research on tumors, brains, hearts, and eyeballs of small animals. With a tendency toward combination of detection of excited light with ultrasound detection, a photoacoustic imaging system may easily be integrated with a conventional ultrasound imaging system after undergoing only a slight modification such as removal of an ultrasound transmission function and addition of a radio frequency (RF) data collection function). Due to its sharing of an acoustic detector, the integrated system may provide advantages of a traditional ultrasound imaging system such as portability and real-time imaging capability.

SUMMARY

One or more embodiments of the present invention include a photoacoustic probe and a photoacoustic diagnostic apparatus configured to provide information as to whether light is irradiated.

Additional aspects will be set forth in part in the description which follows and, in part, will be apparent from the description, or may be learned by practice of the presented embodiments.

According to one or more embodiments of the present invention, a photoacoustic probe includes a light irradiation unit for irradiating first light that is used for photoacoustic imaging on an object and an indicator for providing information about whether the first light is irradiated by using the first light.

The photoacoustic probe may further include a wavelength converter for converting the first light to second light having a different wavelength than the first light, The indicator may output the second light.

The second light may have a wavelength range including a wavelength range that can pass through a filter that blocks the first light.

The wavelength range of the second light may include a wavelength range of visible light.

The second light may have a longer wavelength than the first light.

The wavelength converter may include a fluorescent material.

The second light may have a shorter wavelength than the first light.

The wavelength converter may include a nonlinear crystal material.

The photoacoustic probe may further include: a light source for providing the first light and a light delivery unit for delivering the first light from the light source to the light delivery unit and the indicator.

The light delivery unit may include at least one optical fiber.

The light delivery unit may have one end connected to the light source and the other end connected to the light irradiation unit, and the indicator may be disposed on a side of the light irradiation unit.

The light delivery unit may include a first light delivery unit for delivering a portion of the first light to the light irradiation unit and a second light delivery unit for delivering the remaining portion of the first light to the indicator.

The first light delivery unit may have one end connected to the light source and the other end connected to the light irradiation unit, and the second light delivery unit may have one end connected to the light source and the other end connected to the indicator.

The photoacoustic probe may further include an optical sensor for detecting the first light, and the indicator may output the information about whether the first light is irradiated based on the result of detection output from the optical sensor.

The information may include at least one of an image, a text, and an acoustic sound.

The photoacoustic probe may further include a transducer that receives acoustic waves generated from the object by absorbing the first light and converts the acoustic waves into electrical signals, According to one or more embodiments of the present invention, a photoacoustic diagnostic apparatus includes: a photoacoustic probe including a light irradiation unit for irradiating first light that is used for photoacoustic imaging on an object and a transducer for receiving acoustic waves corresponding to the first light and converting the acoustic waves into electrical signals; a signal processor that processes the electrical signals received from the photoacoustic probe and generates a photoacoustic image; and an indicator for providing information about whether the first light is irradiated by using the first light.

The indicator may emit second light having a different wavelength than the first light.

The apparatus may further include a wavelength converter for converting the first light to the second light.

The wavelength converter may include at least one of a fluorescent material and a nonlinear crystal material.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Exemplary embodiments will now be described more fully hereinafter with reference to the accompanying drawings. In the drawings, reference numerals refer to like elements throughout, and repeated descriptions thereof are omitted here.

In the present specification, an "object" may include a person or an animal, or a part of a person or an animal. For example, the object may include the liver, the heart, the womb, the brain, a breast, the abdomen, or a blood vessel. Furthermore, a "user" refers to a medical professional, such as a doctor, a nurse, a medical laboratory technologist, and an engineer who repairs a medical apparatus, but the user is not limited thereto. Expressions such as "at least one of," when preceding a list of elements, modify the entire list of elements and do not modify the individual elements of the list.

Figure 1:
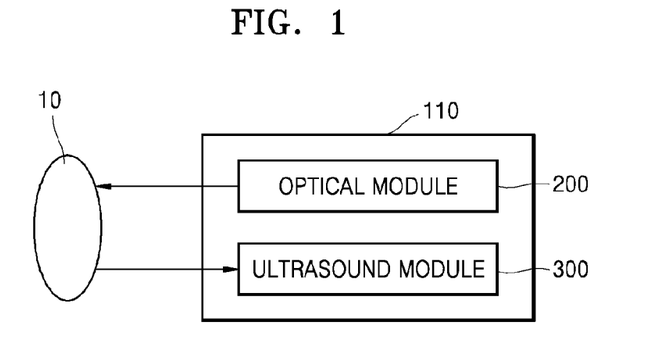
FIG. 1 is a block diagram of a photoacoustic probe.

FIG. 1 is a block diagram of a photoacoustic probe 110. The photoacoustic probe 110 is configured to irradiate light on an object 10 and receive acoustic waves (e.g., ultrasound waves) generated from the object 10 by absorbing energy of the light. To do so, the photoacoustic probe 110 includes an optical module 200 for irradiating light on the object 200 and an ultrasound module 300 for receiving acoustic waves (e.g., ultrasound waves) and converting them into electrical signals. The photoacoustic probe 110 may irradiate light on the object 10 and receive acoustic waves therefrom while moving along the object 10 with its surface being in contact with the object 10.

During manufacturing of the photoacoustic probe 110, the optical module 200 may be integrated with the ultrasound module 300, but the present invention is not limited thereto. The optical module 200 and the ultrasound module 300 may be fabricated separately and then combined together. The optical module 200 and the ultrasound module 300 may be detached from each other. Due to this configuration, the ultrasound module 300 may operate for ultrasound imaging independently, and for photoacoustic imaging only when being combined with the optical module 200. Alternatively, even when the optical module 200 is assembled with the ultrasound module 300, the photoacoustic probe 110 may operate for ultrasound imaging according to a user command as well as for photoacoustic imaging.

The photoacoustic probe 110 necessitates the use of light for photoacoustic imaging. In general, light that is used in photoacoustic imaging is classified as critically dangerous to a human body, and may cause irrevocable accidents such as blindness, burning, and fires. Thus, a lot of care and attention is required when using the photoacoustic probe 110. It is also desirable for a user to recognize actual irradiation of light because this may allow the user to intentionally take special care in using the photoacoustic probe 110. To achieve this, the photoacoustic probe 110 according to an embodiment of the present invention may be configured to output information about irradiation of light.

Figure 2A:
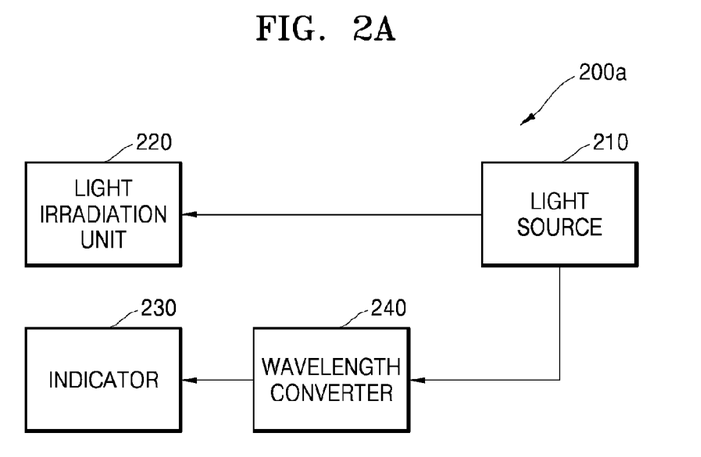
FIG. 2A is a block diagram of a photoacoustic probe according to an exemplary embodiment of the present invention.

FIG. 2A is a block diagram of an optical module 200a according to an exemplary embodiment of the present invention. Referring to FIG. 2A, the optical module 200a according to the present embodiment includes a light source 210 for providing first light that is used for photoacoustic imaging, a light irradiation unit 220 for irradiating the first light on the object (10 in FIG. 1), and an indicator 230 for providing information as to whether the light irradiation unit 220 irradiates the first light by using the first light. The optical module 200a may further include a wavelength converter 240 for converting the first light into second light having a different wavelength than the first light.

The light source 210 may provide light so as to induce acoustic waves from the object 10. The light source 210 may include a laser diode for generating laser light. The laser may be a pulsed laser, and have a nano-sized or pico-sized pulse width. The laser may be a continuous laser. For example, light provided by the light source 210 may have a wavelength range of about 500 nm to about 1500 nm. The light source 210 may provide light having a single central wavelength or a plurality of central wavelengths.

The light irradiation unit 220 may receive first light from the light source 210 and irradiate the first light on the object 10. The light irradiation unit 220 may receive the first light from the light source 210 via an optical fiber (not shown), and the light source 210 may or may not apply the first light to the light irradiation unit 220. In other words, the light irradiation unit 220 may or may not irradiate the first light on the object 10. Furthermore, the light irradiation unit 220 may incorporate a structure for diffusing the first light. When being irradiated with the first light, the object undergoes a temperature increase and a thermal expansion by absorbing the first light and generates acoustic waves (e.g., ultrasound waves).

The indicator 230 may provide information on whether the light irradiation unit 220 irradiates the first light by using the first light. Light having different wavelength ranges according to the object 10 may be used in photoacoustic imaging. The first light may include different wavelength ranges such as visible light that can be seen by a user's eyes and infrared light that cannot be seen directly by the user's eyes. Since light that is used in photoacoustic imaging is so dangerous, the user may wear safety goggles. In general, safety goggles may include a filter for blocking emitted light. For this reason, a user wearing safety goggles may have difficulty in recognizing whether the light irradiation unit 220 actually irradiates the light. To solve this problem, the indicator 230 may output light whose irradiation can be identified even by a user who wears safety goggles. Furthermore, the light output by the indicator 230 may be visible light that is visible to the user's eyes.

Thus, the optical module 200a may include the wavelength converter 240 for converting first light into second light having a different wavelength than the first light. The second light may have a wavelength range that can pass through a filter for blocking the first light, e.g., a filter that is used for safety goggles. Furthermore, the second light may have a wavelength range of visible light that can be seen by the user.

The wavelength converter 240 may convert first light into second light having a longer wavelength than the first light. The wavelength converter 240 may include a fluorescent material that absorbs the first light and then emits the second light having a longer wavelength than the first light. For example, if the light irradiation unit 220 irradiates near-green light having a wavelength of about 500 nm, the user may wear safety goggles that block the light with a wavelength of about 500 nm. The wavelength converter 240 may include a fluorescent material that absorbs the light with a wavelength of about 500 nm and then emits light with a wavelength of about 600 nm that is longer than the light with a wavelength of about 500 nm. Thus, the light with a wavelength of about 600 nm may then be output through the indicator 230, so that the user may identify whether the light irradiation unit 220 irradiates light even while wearing the safety goggles that block the near-green light of about 500 nm.

Alternatively, the wavelength converter 240 may convert first light into second light having a shorter wavelength than the first light. The wavelength converter 240 may contain a nonlinear crystal material that absorbs the first light and emits the second light. In detail, the nonlinear crystal material may be lithium niobate ($LiNbO_3$), potassium titanyl phosphate ($KTP=KTiOPO_4$), or lithium triborate ($LBO=LiB_3O_5$).

For example, if the light irradiation unit 220 irradiates infrared light having a wavelength of about 1064 nm that cannot be seen directly by a user's eyes, the user may wear safety goggles that block the wavelength of about 1064 nm. The wavelength converter 240 may convert the infrared light into green light having a wavelength of about 532 nm that is half the wavelength of the infrared light. Thus, the green light with the wavelength of about 532 nm may then be output through the indicator 230, so that the user may identify whether the light irradiation unit 220 irradiates light even while wearing the safety goggles that block the infrared light of about 1064 nm.

Furthermore, the wavelength converter 240 may also be designed as a combination of a device for converting incident light into light having a shorter wavelength than the incident light and a device for converting the resulting light into light having a longer wavelength than the resulting light. For example, if the light irradiation unit 220 irradiates light having a wavelength of about 700 nm, the wavelength converter 240 may have a nonlinear crystal material and a fluorescent material sequentially arranged. The nonlinear crystal material is used for converting the wavelength of light that is incident in a light propagation direction to a shorter wavelength, and the fluorescent material is used for converting the wavelength of incident light to a longer wavelength. In detail, the light having a wavelength of about 700 nm may be converted to light having a wavelength of about 350 nm as it passes through the nonlinear crystal material. The light having a wavelength of about 350 nm may be converted again to light having a wavelength of about 400 nm to about 500 nm as it passes through the fluorescent material. Thus, the light having a wavelength of about 400 nm to about 500 nm may be output through the indicator 230 so that the user may identify whether the light irradiation unit 220 irradiates light even while wearing the safety goggles that block the light having a wavelength of about 700 nm.

Figure 2B:
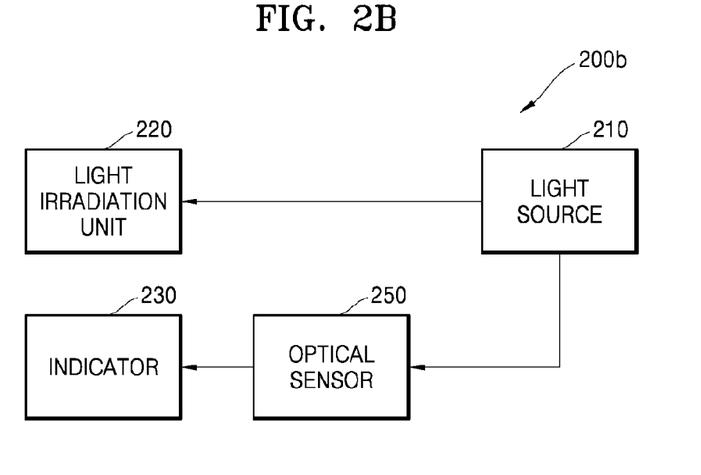
FIG. 2B is a block diagram of an optical module according to another exemplary embodiment of the present invention.

FIG. 2B is a block diagram of an optical module 200b according to another exemplary embodiment of the present invention. The optical module 200b according to the present embodiment is different from the optical module 200a of FIG. 2A in that the optical module 200b includes an optical sensor 250 for detecting first light and converting the first light into an electrical signal instead of the wavelength converter 240, and that the indicator 230 may output information based on the electrical signal (the result detected by the optical sensor 250) received from the optical sensor 250. The indicator 230 may be an image or text that can be perceived by a user's eyes or an acoustic sound that can be detected by a user's ear. The optical sensor 250 may be disposed along a path that light travels, e.g., within the light irradiation unit 220. When the optical sensor 250 is used to detect irradiation of light, the indicator 230 may be implemented in various ways.

Figure 3:
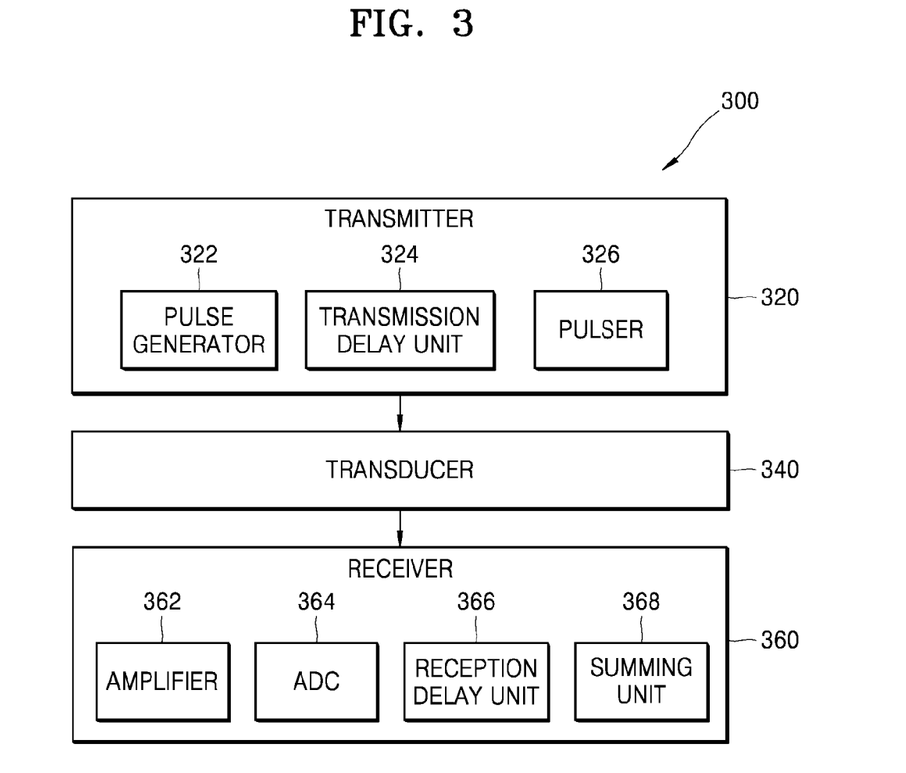
FIG. 3 is a block diagram of an ultrasound module according to an exemplary embodiment of the present invention.

FIG. 3 is a block diagram of an ultrasound module 300 according to an exemplary embodiment of the present invention. Referring to FIG. 3, the ultrasound module 300 according to the present embodiment includes a transmitter 320, a transducer 340, and a receiver 360.

The transmitter 320 supplies a driving signal to the transducer 340. The transmitter 320 may include a pulse generator 322, a transmission delay unit 324, and a pulser 326. The pulse generator 322 generates rate pulses for forming transmission ultrasound waves based on a predetermined pulse repetition frequency (PRF). The transmission delay unit 324 applies a delay time for determining transmission directionality to the rate pulses. The rate pulses to which the delay time is applied correspond to a plurality of elements included in the transducer 340, respectively. The pulser 326 applies a driving signal (or a driving pulse) to the transducer 340 in a timing corresponding to each rate pulse to which a delay time is applied. The plurality of elements may be arranged in a one-dimensional (1D) or two-dimensional (2D) array.

The transducer 340 transmits ultrasound waves to the object (10 in FIG. 1) in response to a driving signal that is supplied by the transmitter 320 and receives ultrasound echo signals reflected from the object 10. The transducer 340 includes the plurality of elements for converting electrical signals into acoustic energy (or vice versa).

The transducer 340 may be realized as a piezoelectric micromachined ultrasonic transducer (pMUT), a capacitive micromachined ultrasonic transducer (cMUT), a magnetic micromachined ultrasonic transducer (mMUT), or an optical ultrasonic detector. The pMUT and the cMUT convert ultrasound waves into electrical signals and electrical signals back into ultrasound waves due to a change in pressure caused by vibration and a change in capacitance, respectively. The mMUT and the optical ultrasonic detector convert ultrasound waves into electrical signals and electrical signals back into ultrasound waves due to a change in magnetic field and a change in optical properties, respectively.

The receiver 360 processes signals received from the transducer 340 to generate ultrasound data and includes an amplifier 362, an analog-to-digital converter (ADC) 364, a reception delay unit 366, and a summing unit 368.

The amplifier 362 amplifies signals received from the transducer 340, and the ADC 364 performs analog-to-digital conversion on the amplified signals. The reception delay unit 366 applies a delay time for determining reception directionality to the digital signals output from the ADC 364, and the summing unit 368 generates ultrasound data by summing the signals processed by the reception delay unit 366.

While the ultrasound module 300 necessarily includes the transducer 340, at least some of the components in the transmitter 320 and the receiver 360 may be included in another device. For example, the ultrasound module 300 may not include the summing unit 368 of the receiver 360. Furthermore, in generating photoacoustic images, the transmitter 320 of the ultrasound module 300 may not operate, or the ultrasound module 300 may not include the transmitter 320 itself.

When ultrasound waves are generated from the object 10 by absorbing light, the transducer 340 receives the ultrasound waves, converts the ultrasound waves into electrical signals, and applies the electrical signals to the receiver 360. The receiver 360 may generate image data based on the electrical signals, and the image data is reconstructed to form a photoacoustic image.

Figure 4:
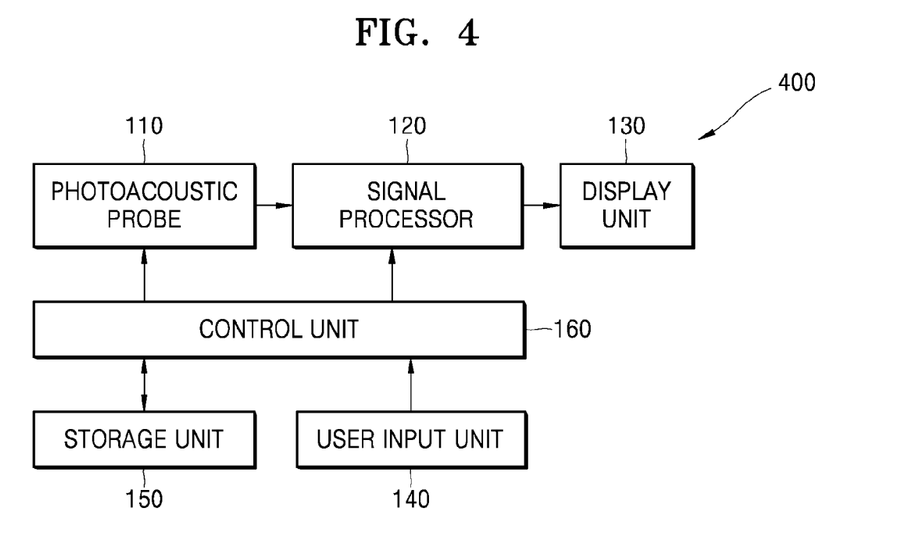
FIG. 4 is a block diagram of a photoacoustic diagnostic apparatus according to an exemplary embodiment of the present invention.

FIG. 4 is a block diagram of a photoacoustic diagnostic apparatus 400 according to an exemplary embodiment of the present invention. Referring to FIG. 4, the photoacoustic diagnostic apparatus 400 according to the present embodiment includes a photoacoustic probe 110 for irradiating light on the object (10 in FIG. 1) and receiving ultrasound waves from the object 10, a signal processor 120 for processing signals applied by the photoacoustic probe 110 and generating an image, a display unit 130 for displaying the image, a user input unit 140 for receiving a user command, a storage unit 150 for storing various types of information, and a control unit 160 for controlling overall operations of the photoacoustic diagnostic apparatus 400.

As described above, the photoacoustic probe 110 is configured to irradiate light on the object 10 and receive ultrasound waves generated from the object 10. The same descriptions as already presented are omitted.

The signal processor 120 may process ultrasound data generated by the photoacoustic probe 110 and generate a photoacoustic image. Since the photoacoustic image is generated by using a currently implementable method, a detailed description thereof is omitted here. The signal processor 120 may also produce an ultrasound image by using a currently implementable method, so a detailed description thereof is omitted.

The display unit 130 displays information that is processed by the photoacoustic diagnostic apparatus 400. For example, the display unit 130 may display a photoacoustic image generated by the signal processor 120 as well as a graphical user interface (GUI) that appears in order to request a user input.

The display unit 130 may include at least one of a liquid crystal display (LCD), a thin film transistor-LCD (TFT-LCD), an organic light-emitting diode (OLED), a flexible display, a three-dimensional (3D) display, and an electrophoretic display. The photoacoustic diagnostic apparatus 400 may include two or more display units 130 according to embodiments of the present invention.

The user input unit 140 refers to a means via which a user inputs data for controlling the photoacoustic diagnostic apparatus 400. The user input unit 195 may include a keypad, a mouse, a touch panel, and a track ball. The user input unit 140 is not limited thereto, and may further include various other input elements such as a jog wheel and a jog switch.

The touch panel may be constructed to detect both a real touch where a pointer actually touches a screen and a proximity touch where the pointer approaches the screen while being separated from the screen by less than a predetermined distance. In the present specification, the term 'pointer' means a tool for touching a particular portion on or near the touch panel. Examples of the pointer may include a stylus pen and a portion of a user's body such as fingers.

In addition, the touch panel may be realized as a touch screen that forms a layer structure with the display unit 130. In this case, the touch screen may be implemented as various types such as capacitive overlay, resistive overlay, infrared beam, surface acoustic wave, integral strain gauge, and piezoelectric touch screens. The touch screen is very useful because it functions as both the display unit 130 and the user input unit 140.

Although not shown in FIG. 4, various sensors may be disposed within or near the touch panel so as to sense a touch. A tactile sensor is an example of the sensors for sensing a touch. The tactile sensor is used to sense a touch of a particular object to the same or greater degree than the degree to which a human can sense the touch. The tactile sensor may detect various information including the toughness of a contact surface, the hardness of an object to be touched, and the temperature of a point to be touched.

A proximity sensor is another example of the sensors for sensing a touch. The proximity sensor means a sensor that senses the presence of an object that is approaching or is located near a predetermined detection surface by using the force of an electromagnetic field or infrared light without any mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor.

The storage unit 150 stores various types of information that are processed by the photoacoustic diagnostic apparatus 400. For example, the storage unit 150 may store medical data related to diagnosis of the object 10, such as images, and algorithms or programs that are executed in the photoacoustic diagnostic apparatus 400.

The storage unit 150 may include at least one storage medium from among a flash memory-type storage medium, a hard disk-type storage medium, a multimedia card micro-type storage medium, card-type memories (e.g., an SD card, an XD memory, and the like), a Random Access Memory (RAM), a Static Random Access Memory (SRAM), a Read-Only Memory (ROM), an Electrically Erasable Programmable ROM (EEPROM), a PROM, a magnetic memory, a magnetic disc, and an optical disc. The photoacoustic diagnostic apparatus 400 may utilize a web storage or a cloud server that functions as the storage unit 150 online.

The control unit 160 controls the overall operations of the photoacoustic diagnostic apparatus 400. In detail, the control unit 160 may control operations of the photoacoustic probe 110, the signal processor 120, and the display unit 130. For example, the control unit 160 may control the signal processor 120 to generate an image by using a user command received via the user input unit 140 or programs stored in the storage unit 150. The control unit 160 may also control the display unit 130 to display the image generated by the signal processor 120.

Figure 5:
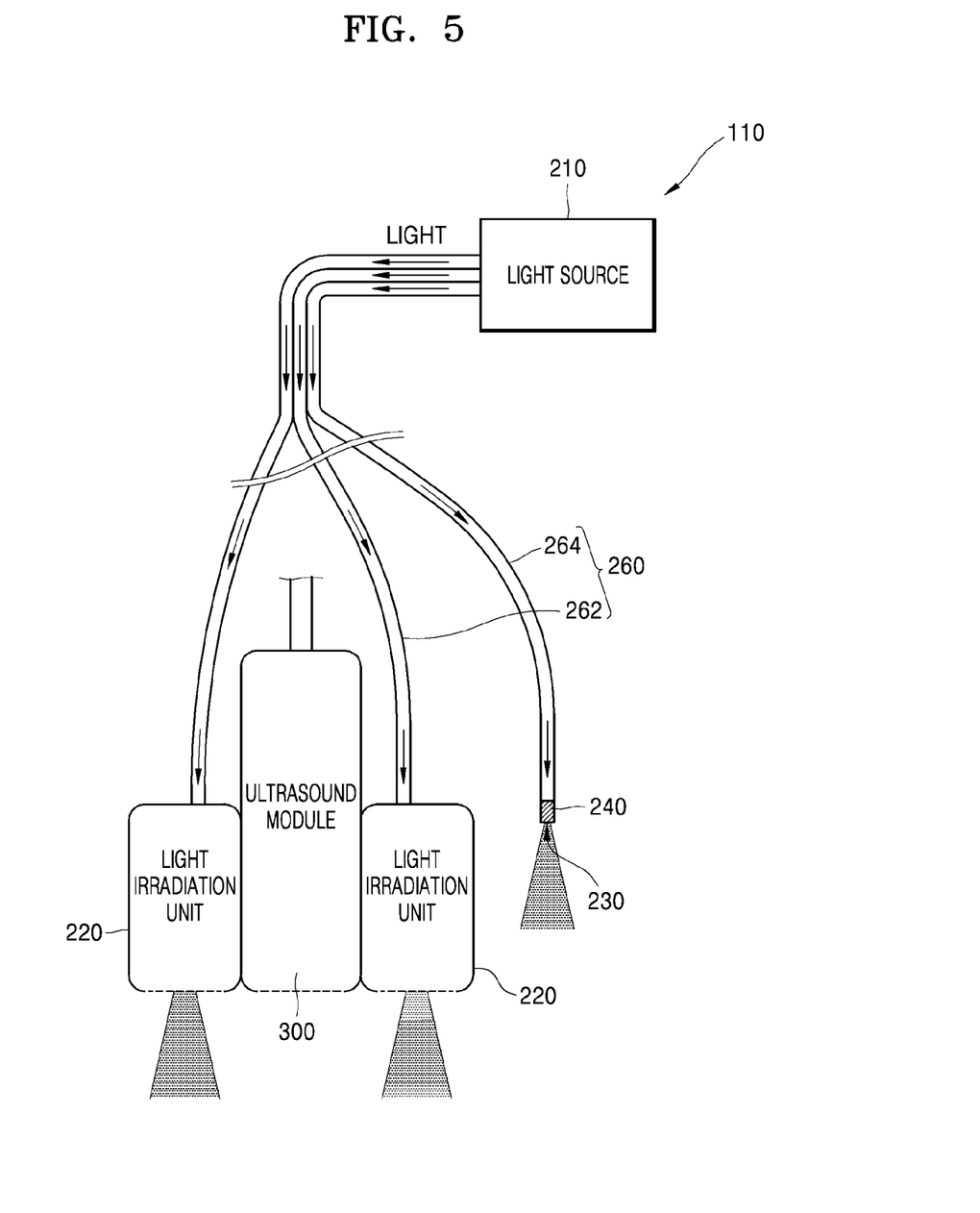
FIG. 5 schematically illustrates a photoacoustic probe according to an exemplary embodiment of the present invention.

FIG. 5 schematically illustrates a photoacoustic probe 110 according to an exemplary embodiment of the present invention. Referring to FIG. 5, two light irradiation units 220 are disposed around the ultrasound module 300, i.e., on either side of an ultrasound module 300. However, the present invention is not limited thereto, and the photoacoustic probe 110 may include a single or three or more light irradiation units 220. First light emitted by a light source 210 may be transmitted to the light irradiation units 220 and an indicator 230 through a light delivery unit 260. The light delivery unit 260 may include at least one optical fiber. For example, the light delivery unit 260 may include a first light delivery unit 262 for delivering a portion of the first light to the light irradiation unit 220 and a second light delivery unit 264 for delivering the remaining portion of the first light to the indicator 230. In detail, the first light delivery unit 262 has one end connected to the light source 210 and the other end connected to the light irradiation units 220. The second light delivery unit 264 has one end connected to the light source 210 and the other end connected to the indicator 230. Furthermore, a wavelength converter 240 may be disposed in the second light delivery unit 264 so as to convert the first light to second light that will be emitted to the outside through the indicator 230.

Figure 6:
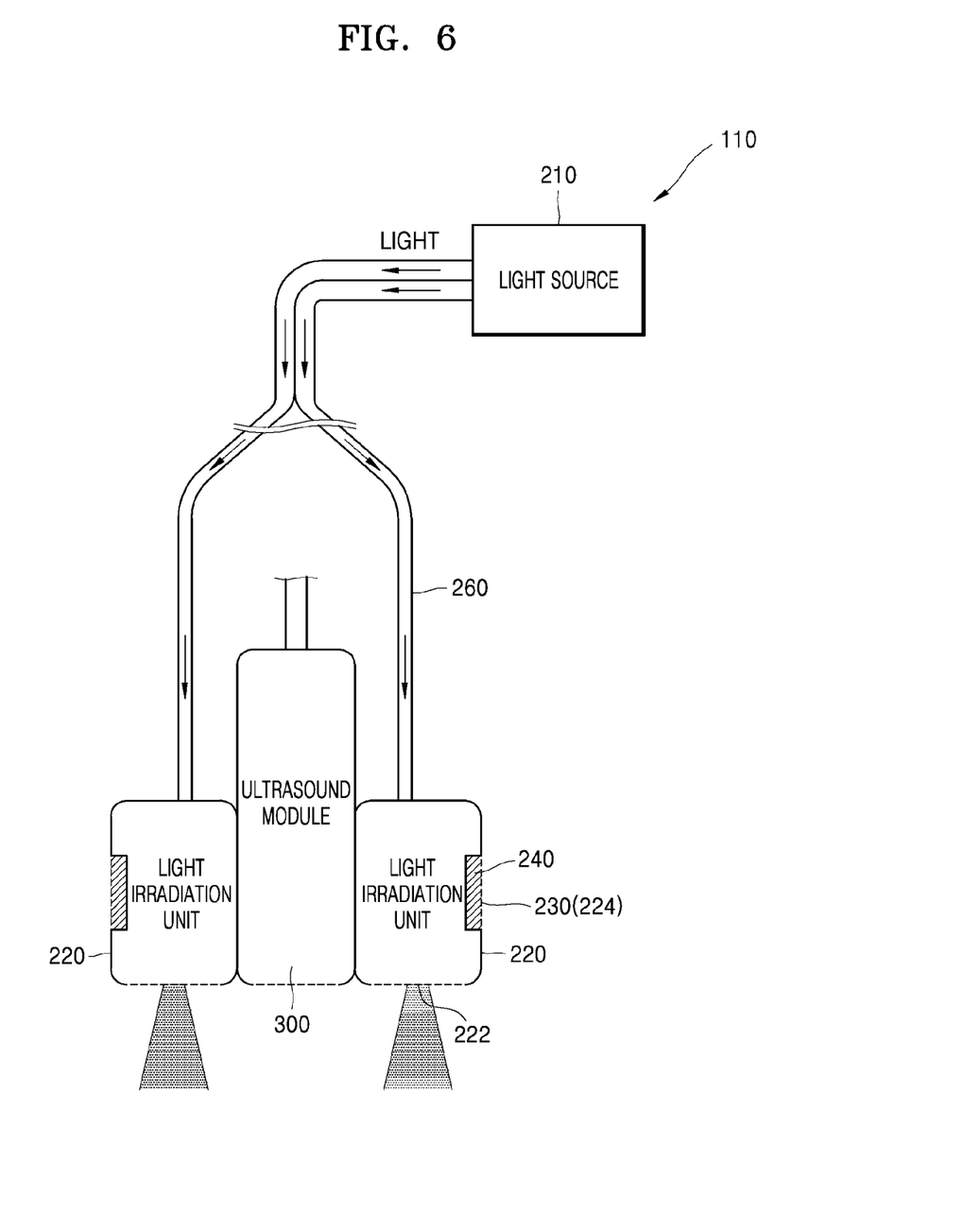
FIG. 6 illustrates a photoacoustic probe according to another exemplary embodiment of the present invention.

FIG. 6 illustrates a photoacoustic probe 110 according to another exemplary embodiment of the present invention. The photoacoustic probe 110 according to the present embodiment differs from the photoacoustic probe 110 of FIG. 5 in that it does not include a separate second light delivery unit for delivering first light to an indicator 230 and that the indicator 230 is disposed in a light irradiation unit 230. For example, the light irradiation unit 220 has one end connected to a light delivery unit 260 and the other end connected to a first opening 222. The light irradiation unit 220 may irradiate light on the object 10 through the first opening 222. The indicator 230 may be formed as a second opening 224 in a side of the light irradiation unit 220. At least a part of a wavelength converter 240 may overlap with the second opening 224. Thus, a portion of first light applied to the light irradiation unit 220 may undergo wavelength conversion as it enters the wavelength converter 240 and then be output through the second opening 224 that functions as the indicator 230.

Figure 7:
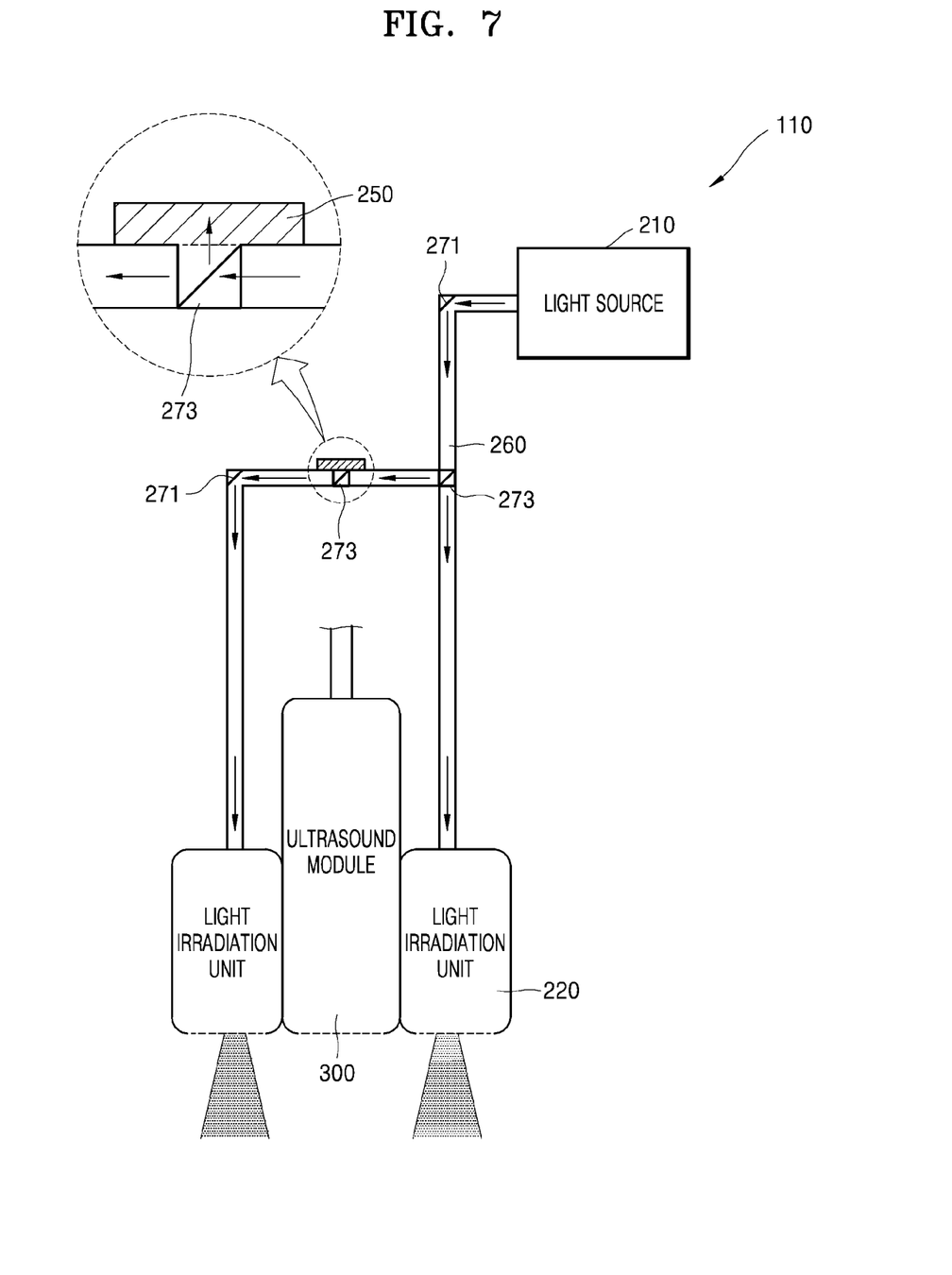
FIG. 7 illustrates a photoacoustic probe according to another exemplary embodiment of the present invention.

FIG. 7 illustrates a photoacoustic probe 110 according to another exemplary embodiment of the present invention. Referring to FIG. 7, a mirror 271 and a beam splitter 273 may also be disposed in a light delivery unit 260 so as to control a path along which light propagates. In addition, at least one optical sensor 250 may be disposed on the light delivery unit 260 and the light irradiation unit 220 so as to detect light. Although the optical sensor 250 is disposed on a side of the light delivery unit 260, the present invention is not limited thereto, and the optical sensor 250 may be disposed within the light irradiation unit 220 or the light delivery unit 260.

An indicator 230 that has received the result of detection by the optical sensor 250 as an electrical signal may display information about whether the light irradiation unit 220 irradiates light by using various methods. The indicator 230 may be realized as a photodiode. Thus, as the light irradiation unit 220 irradiates light, the indicator 230 may also emit light. In this case, the indicator 230 may emit light in a wavelength range that can be visually perceived even when a user wears safety goggles. In other words, the emitted light may be visible light having a wavelength that does not overlap that of first light. Since the indictor 230 is configured to receive an electrical signal from the optical sensor 250 as described above, it may have less spatial limitations than the indicator (230 in FIG. 5) that emits second light.

Figure 8:
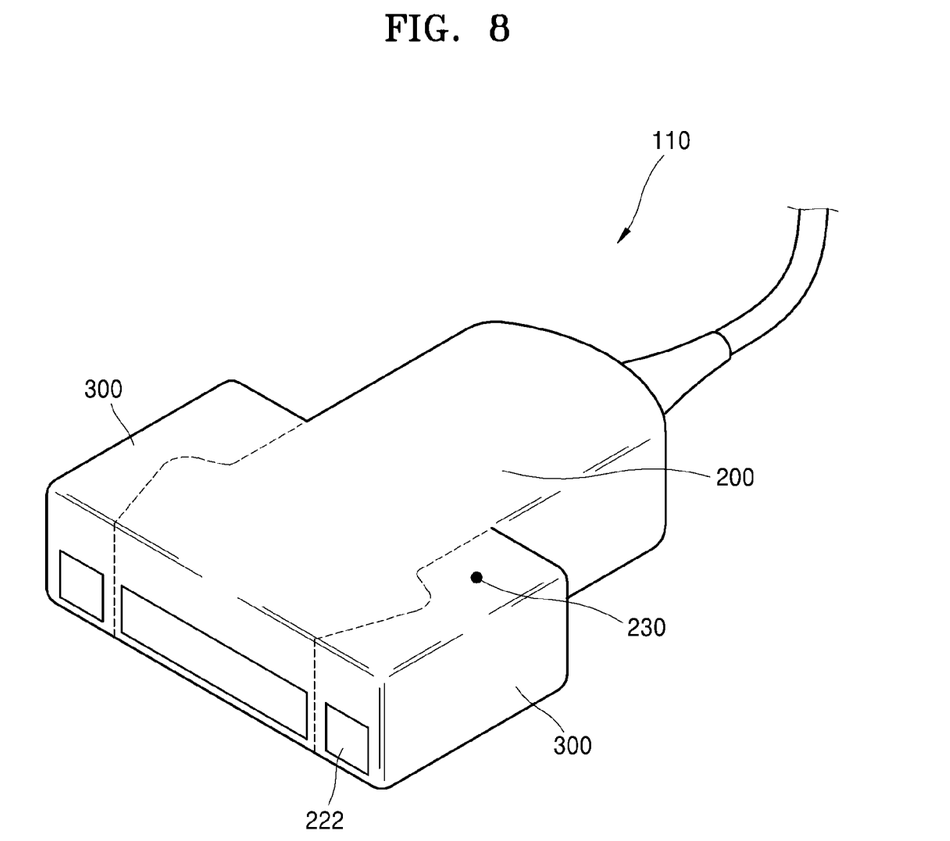
FIGS. 8 through 10 schematically illustrate arrangement of an indicator.
Figure 9:
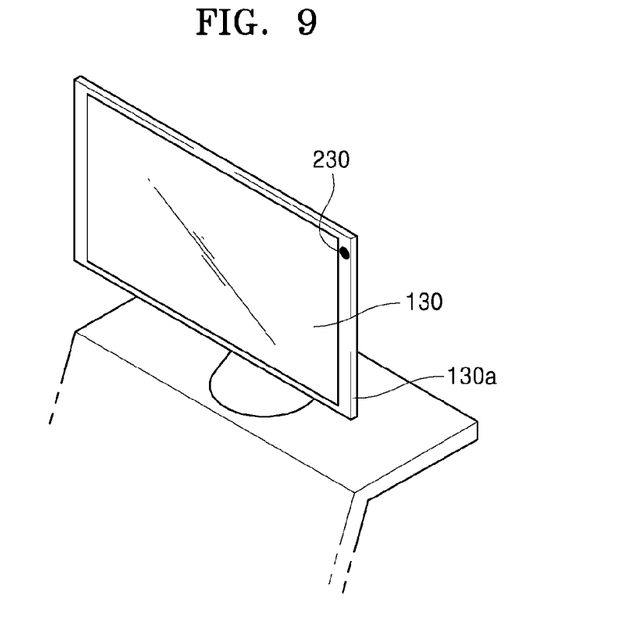
Figure 10:
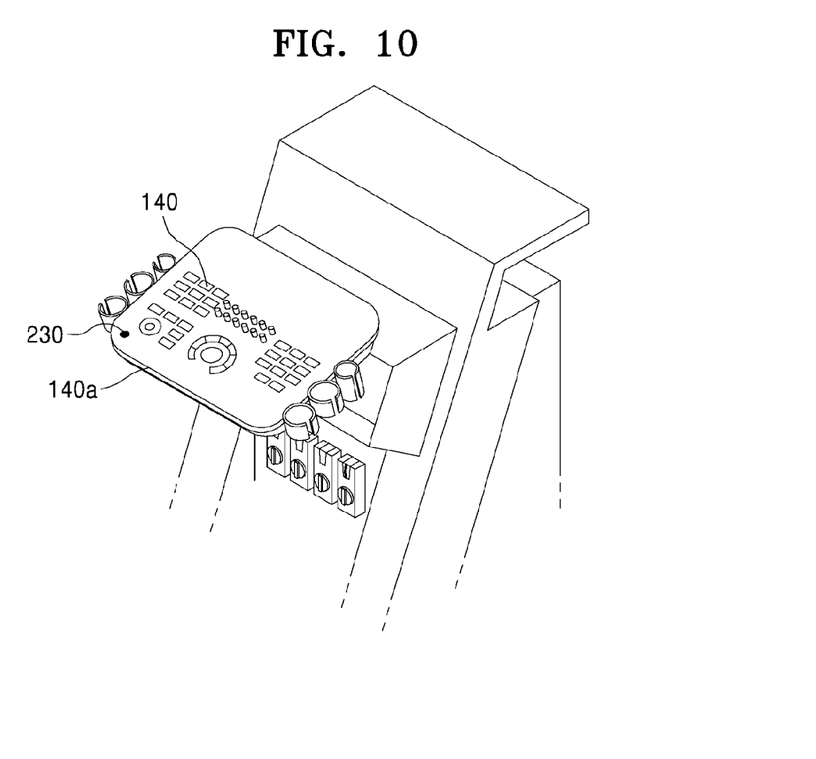

FIGS. 8 through 10 schematically illustrate arrangement of an indicator 230. The indicator 230 as a photodiode may be disposed on the photoacoustic probe 110 as shown in FIG. 8, on a display device 130*a* including a display unit 130 as shown in FIG. 9, and on a manipulation device 140*a* including a user input unit 140 as shown in FIG. 10.

Although not shown in FIGS. 8 through 10, the indicator 230 may also be displayed on a screen of the display unit 130 as a user interface in the form of a text or image. Furthermore, information about irradiation of light may be provided by using a visual output or sounds as an auditory output.

While it is described above that irradiation of light by the light irradiation unit 220 is determined according to whether the light source 210 emits light in response to a user command, the description is provided for convenience of explanation only and not for purposes of limitation. The light source 210 may continuously provide light to the light irradiation unit 220, and the light irradiation unit 220 may selectively irradiate light. In this case, the indicator 230 may be disposed within the light irradiation unit 220.

As described above, according to the one or more of the above embodiments of the present invention, the photoacoustic probe and the photoacoustic diagnostic apparatus are configured to provide information about irradiation of light, thereby allowing user to easily recognize irradiation of light. This configuration may also allow the user to easily verify whether a failure to normally produce a photoacoustic image is caused by irradiation of light. Furthermore, the photoacoustic probe and the photoacoustic diagnostic apparatus may easily provide information about irradiation of light by converting a wavelength of emitted light. In addition, the photoacoustic probe and the photoacoustic diagnostic apparatus may convert information about irradiation of light into an electrical signal for provision, thereby allowing various implementations.

While one or more embodiments of the present invention have been described with reference to the figures, it should be understood that the exemplary embodiments described therein should be considered in a descriptive sense only and not for purposes of limitation. Thus, it will be understood by those of ordinary skill in the art that various changes in form and details may be made therein without departing from the spirit and scope of the present invention as defined by the following claims. All modifications and substitutions within the scope of the appended claims and their equivalents will be construed as being included in the present invention.

What is claimed is:

1. A photoacoustic probe configured to irradiate light on an object, comprising:
   a light source providing a first light;
   a wavelength converter on a housing of the photoacoustic probe and configured to receive a portion of the first light provided by the light source and convert the received portion of the first light into a second light having a different wavelength than the first light;
   an opening disposed on the housing of the photoacoustic probe, receiving the second light from the wavelength converter, and outputting the second light itself to a user, the opening overlapping with the wavelength converter; and a light irradiator receiving a remaining portion of the first light provided by the light source and irradiating the remaining portion of the first light on the object, wherein the remaining portion of the first light and the second light are simultaneously output out of the housing of the photoacoustic probe such that the remaining portion of the first light is used for photoacoustic imaging and the second light is used for visibly indicating to the user whether the photoacoustic probe is irradiating the remaining portion of the first light on the object.

2. The photoacoustic probe of claim 1, wherein the wavelength of the second light comprises a wavelength range of visible light.

3. The photoacoustic probe of claim 1, wherein the second light has a longer wavelength than the first light.

4. The photoacoustic probe of claim 3 wherein the wavelength converter comprises a fluorescent material.

5. The photoacoustic probe of claim 1, wherein the second light has a shorter wavelength than the first light.

6. The photoacoustic probe of claim 5, wherein the wavelength converter comprises a nonlinear crystal material.

7. The photoacoustic probe of claim 1, further comprising:
a light deliverer receiving the first light provided by the light source and delivering the first light from the light source to the light irradiator and the wavelength converter.

8. The photoacoustic probe of claim 7, wherein the light deliverer comprises at least one optical fiber.

9. The photoacoustic probe of claim 7, wherein the light deliverer has one end connected to the light source and the other end connected to the light irradiator, and
wherein the indicator is disposed on a side of the light irradiator.

10. The photoacoustic probe of claim 7, wherein the light deliverer comprises a first light deliverer for delivering the portion of the first light to the wavelength converter and a second light deliverer for delivering the remaining portion of the first light to the light irradiator.

11. The photoacoustic probe of claim 10, wherein the first light deliverer has one end connected to the light source and the other end connected to the wavelength converter, and
wherein the second light deliverer has one end connected to the light source and the other end connected to the light irradiator.

12. The photoacoustic probe of claim 1, further comprising a transducer that receives acoustic waves generated from the object by absorbing the first light and converts the acoustic waves into electrical signals.

13. A photoacoustic diagnostic apparatus comprising:
a light source providing a first light;
a wavelength converter on a housing of a photoacoustic probe and configured to receive a portion of the first light provided by the light source and convert the received portion of the first light into a second light having a different wavelength than the first light;
a light irradiator receiving a remaining portion of the first light provided by the light source and irradiating the remaining portion of first light on the object, and a transducer receiving acoustic waves corresponding to the remaining portion of the first light and converting the acoustic waves into electrical signals;
a signal processor that processes the electrical signals received from the photoacoustic probe and generates a photoacoustic image; and
an opening disposed on the housing of the photoacoustic probe, receiving the second light from the wavelength converter, and outputting the second light itself to a user, the opening overlapping with the wavelength converter,
the remaining portion of the first light and the second light are simultaneously output out of the housing of the photoacoustic probe such that the remaining portion of the first light is used for photoacoustic imaging and the second light is used for visibly indicating to the user whether the photoacoustic probe is irradiating the remaining portion of the first light on the object.

14. The apparatus of claim 13, wherein the wavelength converter comprises at least one of a fluorescent material and a nonlinear crystal material.

15. The apparatus of claim 1, wherein the opening outputs the second light itself such that the second light travels to the user through a first light path, and
wherein the light irradiator irradiates the remaining portion of the first light on the object such that the remaining portion of the first light travels to the object through a second light path different from the first light path.

16. The apparatus of claim 13, wherein the opening outputs the second light itself such that the second light travels to the user through a first light path, and
wherein the light irradiator irradiates the remaining portion of the first light on the object such that the remaining portion of the first light travels to the object through a second light path different from the first light path.

* * * * *